(12) United States Patent
Nakaji et al.

(10) Patent No.: US 9,545,525 B2
(45) Date of Patent: Jan. 17, 2017

(54) DOSIMETRICALLY CUSTOMIZABLE BRACHYTHERAPY CARRIERS AND METHODS THEREOF IN THE TREATMENT OF TUMORS

(71) Applicant: GammaTile LLC, Gilbert, AZ (US)

(72) Inventors: Peter Nakaji, Phoenix, AZ (US); David Brachman, Phoenix, AZ (US); Heyoung McBride, Phoenix, AZ (US); Emad Youssef, Peoria, AZ (US); Theresa Thomas, Gilbert, AZ (US)

(73) Assignee: GammaTile LLC, Gilbert, AZ (US)

( * ) Notice: Subject to any disclaimer, the term of this patent is extended or adjusted under 35 U.S.C. 154(b) by 0 days.

(21) Appl. No.: 14/703,244

(22) Filed: May 4, 2015

(65) Prior Publication Data

US 2015/0321024 A1 Nov. 12, 2015

Related U.S. Application Data

(63) Continuation of application No. 13/460,792, filed on Apr. 30, 2012, now Pat. No. 9,022,915.

(Continued)

(51) Int. Cl.
*A61N 5/10* (2006.01)

(52) U.S. Cl.
CPC .............. *A61N 5/1014* (2013.01); *A61N 5/103* (2013.01); *A61N 5/1007* (2013.01);
(Continued)

(58) Field of Classification Search
CPC ............... A61N 2005/1009; A61N 2005/1024; A61N 2005/1011; A61N 2005/101; A61N 2005/1023; A61N 2005/1025; A61N 5/1014; A61N 5/1007; A61N 5/103; A61N 5/1027
(Continued)

(56) References Cited

U.S. PATENT DOCUMENTS

| D244,393 S | 5/1977 | Collica et al. |
|---|---|---|
| 4,706,652 A | 11/1987 | Horowitz |

(Continued)

FOREIGN PATENT DOCUMENTS

| DE | 613 528 | 5/1935 |
|---|---|---|
| EP | 0 906 769 A2 | 4/1999 |

(Continued)

OTHER PUBLICATIONS

Cole, P.D., et al., "A comparative long-term assessment of four soft tissue supplements". Anesthetic Surg J. 31(6). 674-681, 2011.
(Continued)

*Primary Examiner* — Christine H Matthews
*Assistant Examiner* — Kaylee Wilson
(74) *Attorney, Agent, or Firm* — Knobbe, Martens, Olson & Bear LLP

(57) ABSTRACT

Brachytherapy radioisotope carrier systems and methodology for providing real-time customized brachytherapy treatment to subjects with tumors difficult to control using conventional radiation therapy techniques. The invention generally relates to devices, methods and kits for providing customized radionuclide treatments, to help cure, slow progression or regrowth, or ameliorate the symptoms associated with tumors.

15 Claims, 12 Drawing Sheets

Related U.S. Application Data

(60) Provisional application No. 61/480,304, filed on Apr. 28, 2011.

(52) U.S. Cl.
CPC ...... *A61N 5/1027* (2013.01); *A61N 2005/101* (2013.01); *A61N 2005/1009* (2013.01); *A61N 2005/1023* (2013.01); *A61N 2005/1024* (2013.01)

(58) Field of Classification Search
USPC .......................................................... 600/8
See application file for complete search history.

(56) References Cited

U.S. PATENT DOCUMENTS

| | | | |
|---|---|---|---|
| 4,754,745 A * | 7/1988 | Horowitz | A61N 5/1007 600/8 |
| 4,946,435 A * | 8/1990 | Suthanthiran | A61K 9/70 600/1 |
| 5,030,195 A | 7/1991 | Nardi | |
| D381,080 S | 7/1997 | Ohata | |
| 5,772,574 A | 6/1998 | Nanko | |
| 5,803,895 A | 9/1998 | Kronholz et al. | |
| 5,840,008 A | 11/1998 | Klein et al. | |
| 5,871,708 A | 2/1999 | Park et al. | |
| D408,957 S | 4/1999 | Sandor | |
| 5,967,966 A | 10/1999 | Kronholz et al. | |
| 5,997,842 A | 12/1999 | Chen | |
| 6,017,482 A | 1/2000 | Anders et al. | |
| D420,452 S | 2/2000 | Cardy | |
| D420,745 S | 2/2000 | Cardy | |
| D420,746 S | 2/2000 | Cardy | |
| D443,061 S | 5/2001 | Bergstrom et al. | |
| 6,248,057 B1 | 6/2001 | Mavity et al. | |
| 6,385,477 B1 | 5/2002 | Werner et al. | |
| 6,450,937 B1 | 9/2002 | Mercereau et al. | |
| 6,512,943 B1 | 1/2003 | Kelcz | |
| 6,712,508 B2 | 3/2004 | Nilsson et al. | |
| D488,864 S | 4/2004 | Fago et al. | |
| 6,787,042 B2 | 9/2004 | Bond et al. | |
| 7,011,619 B1 * | 3/2006 | Lewis | A61N 5/1027 600/8 |
| D561,896 S | 2/2008 | Jones | |
| D580,056 S | 11/2008 | Orthner | |
| D580,057 S | 11/2008 | Ramadani | |
| 8,039,790 B2 | 10/2011 | Cho et al. | |
| D657,474 S | 4/2012 | Dona | |
| D680,649 S | 4/2013 | Jagger et al. | |
| D681,210 S | 4/2013 | Beiriger et al. | |
| D681,812 S | 5/2013 | Farris et al. | |
| D681,813 S | 5/2013 | Jagger et al. | |
| D686,341 S | 7/2013 | Nakaji et al. | |
| D686,744 S | 7/2013 | Nakaji et al. | |
| D686,745 S | 7/2013 | Nakaji et al. | |
| D686,746 S | 7/2013 | Nakaji et al. | |
| D686,747 S | 7/2013 | Nakaji et al. | |
| D686,748 S | 7/2013 | Nakaji et al. | |
| D687,568 S | 8/2013 | Nakaji et al. | |
| D687,966 S | 8/2013 | Nakaji et al. | |
| D687,967 S | 8/2013 | Nakaji et al. | |
| 8,600,130 B2 | 12/2013 | Eriksson Järliden | |
| 8,605,966 B2 | 12/2013 | Eriksson Järliden | |
| 8,825,136 B2 | 9/2014 | Giller et al. | |
| 8,876,684 B1 | 11/2014 | Nakaji et al. | |
| 8,939,881 B2 | 1/2015 | Nakaji et al. | |
| 8,974,364 B1 | 3/2015 | Nakaji et al. | |
| 9,022,915 B2 | 5/2015 | Nakaji et al. | |
| 9,403,033 B1 | 8/2016 | Brachman | |
| 2001/0044567 A1 | 11/2001 | Zamora et al. | |
| 2003/0088141 A1 | 5/2003 | Terwilliger et al. | |
| 2003/0130573 A1 | 7/2003 | Yu et al. | |
| 2003/0208096 A1 | 11/2003 | Tam | |
| 2004/0109823 A1 | 6/2004 | Kaplan | |
| 2004/0116767 A1 | 6/2004 | Lebovic et al. | |
| 2004/0242953 A1 * | 12/2004 | Good | A61K 51/1241 600/7 |
| 2005/0035310 A1 | 2/2005 | Drobnik et al. | |
| 2005/0244045 A1 | 11/2005 | Eriksson | |
| 2006/0063962 A1 | 3/2006 | Drobnik et al. | |
| 2006/0173236 A1 | 8/2006 | White et al. | |
| 2006/0235365 A1 * | 10/2006 | Terwilliger | A61N 5/1027 604/500 |
| 2007/0225544 A1 | 9/2007 | Vance et al. | |
| 2008/0004714 A1 * | 1/2008 | Lieberman | A61B 17/58 623/23.76 |
| 2008/0221384 A1 | 9/2008 | Chi Sing et al. | |
| 2009/0012347 A1 * | 1/2009 | Helle | A61M 37/0069 600/7 |
| 2009/0131735 A1 | 5/2009 | Drobnik et al. | |
| 2009/0253950 A1 | 10/2009 | Rapach et al. | |
| 2010/0056908 A1 | 3/2010 | Giller et al. | |
| 2010/0200778 A1 | 8/2010 | Drobnik et al. | |
| 2010/0228074 A1 | 9/2010 | Drobnik et al. | |
| 2010/0268015 A1 | 10/2010 | Drobnik et al. | |
| 2010/0324353 A1 * | 12/2010 | Helle | A61N 5/1027 600/8 |
| 2011/0013818 A1 | 1/2011 | Eriksson Järliden | |
| 2011/0206252 A1 | 8/2011 | Eriksson Järliden | |
| 2013/0131434 A1 | 5/2013 | Nakaji et al. | |
| 2013/0338423 A1 | 12/2013 | Nakaji et al. | |
| 2014/0275715 A1 | 9/2014 | Brachman et al. | |
| 2014/0316187 A1 | 10/2014 | Nakaji et al. | |
| 2015/0057487 A1 | 2/2015 | Nakaji et al. | |
| 2015/0196778 A1 | 7/2015 | Nakaji et al. | |

FOREIGN PATENT DOCUMENTS

| | | |
|---|---|---|
| JP | H09-028810 | 4/1997 |
| JP | 2007-512112 | 5/2007 |
| JP | 2009-515603 | 4/2009 |
| JP | 2010-536529 | 12/2010 |
| WO | WO 2007/106531 A1 | 9/2007 |

OTHER PUBLICATIONS

International Search Report; International Application No. PCT/US2012/035907, mailed on Sep. 26, 2012; 3 pages.

International Search Report; International Application No. PCT/US2012/035907, mailed on Aug. 30, 2012; 3 pages.

Crepeau, R.H., et al., "Image Processing of Imperfect Protein Arrays: Sectioned Crystals and Tubulin Sheets and Rings". Elec. Microsc. Soc. Amer. Proc. 40:84-87, 1982.

Crepeau, R.H., et al., "Reconstruction of imperfectly ordered zinc-induced tubulin sheets using cross-correlation and real space averaging". Ultramicroscopy, 6, 7-18, 1981.

Dagnew, E., et al., "Management of newly diagnosed single brain metastasis using resection and permanent iodine-125 seeds without initial whole-brain radiotherapy: a two institution experience". Neurosurg Focus. 15; 22(3):E3, 2007.

Delaney, T.F., et al., "Intraoperative dural irradiation by customized 192Iridium and 90yttrium brachytherapy plaques". Int. J. Radiat Oncol Biol Phys. 57(1): 239-245, 2003.

Gutin, P.H., et al., "A coaxial catheter system for afterloading radioactive sources for the interstitial irradiation of brain tumors. Technical note". J. Neurosurg 56: 734-735, 1982.

Gutin, P.H., et al., "Brachytherapy of recurrent tumors of the skull base and spine with iodine-125 sources". Neurosurgery 20:938-945, 1987.

Hamilton, A.J., et al., "The use of gold foil wrapping for radiation protection of the spinal cord for recurrent tumor therapy". Int. J. Radiat Oncol Biol Phys. 32(2):507-511, 1995.

Hilaris, B.S., et al., "Interstitial irradiation for unresectable carcinoma of the lung". Ann Thoracic Surg; 20:491-500, 1975.

Hilaris, B.S., et al., "Intraoperative radiotherapy in stage I and II lung cancer". Semin Surg Oncol. 3:22-32, 1987.

Huang, K., et al., "Surgical resection and permanent iodine-125 brachytherapy for brain metastases". J. Neurooncol. 91:83-93, 2009.

(56) References Cited

OTHER PUBLICATIONS

Jenkins, H.P., et al., "Clinical and experimental observations on the use of a gelatin sponge or foam". Surg 20:124-132, 1946.

Kneschaurek, P. et al.: "Die Flabmethode Zur Intraoperativen Bestrahlung. Öthe Flab-Method for Introperative Radiation Therapy", Strahlentherapie and Oknologie, Uran Und Vogel, Muenchen, DE, vol. 171, No. 2; Feb. 1, 1995, pp. 61-69, XP000610565, ISSN:0179-7158.

Marchese, M.J., et al., "A versatile permanent planar implant technique utilizing iodine-125 seeds imbedded in gelfoam". Int J Radiat Oncol Biol Phys 10:747-751, 1984.

Murphy, M.K., et al., "Evaluation of the new cesim-131 seed for use in low-energy x-ray brachytherapy". Med Phy 31(6): 1529-1538, Jun. 2004.

Nori, D., et al., "Intraoperative brachytherapy using Gelfoam radioactive plaque implants for resected stage III non-small-cell lung cancer with positive margin: A pilot study". J Surg Oncol. 60:257-261, 1995.

Parashar, B., et al., "Cesium-131 permanent seed brachytherapy: Dosimetric evaluation and radiation exposure to surgeons, radiation oncologists, and staff". Brachytherapy. 10:508-511, 2011.

Patel, S., et al., "Permanent iodine-125 interstitial implants for the treatment of recurrent Glioblastoma Multiforme". Neurosurgery 46 (5) 1123-1128, 2000.

Rivard, M.J., "Brachytherapy dosimetry parameters calculated for a 131 Cs source". Med Phys. 34(2): 754-765, 2007.

Rogers, C.L., et al., "Surgery and permanent 125-1 seed paraspinal brachytherapy for malignant tumors with spinal cord compression". Int. J. Radial Oncol Bioi Phys. 54(2): 505-513, 2002.

Wernicke, A.G., et al., "Feasibility and safety of Gliasite brachytherapy in the treatment of CNS tumors following neurosurgical resection". J. Cancer Res Ther. 6(1), 65-74, Jan.-Mar. 2010.

Office Action dated Apr. 2, 2015; European Patent Application No. 12724426.7; 5 pages.

Office Action dated Oct. 30, 2015; European Patent Application No. 12724426.7; 4 pages.

Office Action dated Feb. 9, 2016; Japanese Application No. 2014-508190; 5 pages including english translation.

\* cited by examiner

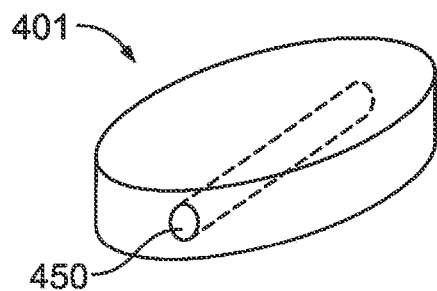
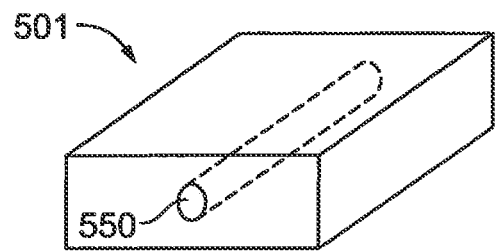
FIG. 4A  FIG. 4B
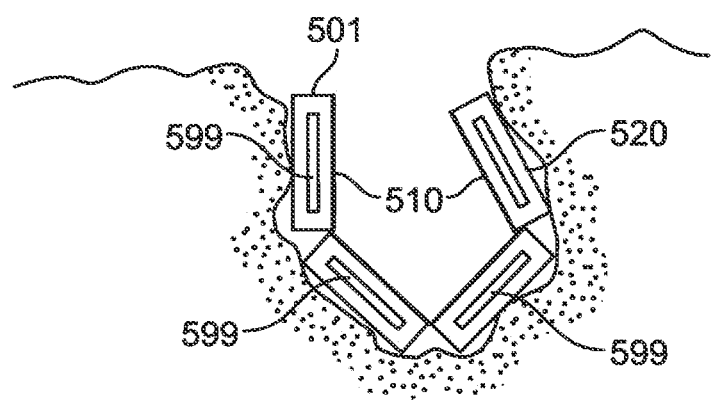
FIG. 5

DOSIMETRICALLY CUSTOMIZABLE BRACHYTHERAPY CARRIERS AND METHODS THEREOF IN THE TREATMENT OF TUMORS

PRIORITY CLAIM

This application is a continuation of U.S. patent application Ser. No. 13/460,792, filed on Apr. 30, 2012, entitled "DOSIMETRICALLY CUSTOMIZABLE BRACHYTHERAPY CARRIERS AND METHODS THEREOF IN THE TREATMENT OF TUMORS", which claims the benefit under 35 U.S.C. §119 of U.S. Provisional Patent Application Ser. No. 61/480,304, filed Apr. 28, 2011, and entitled "DOSIMETRICALLY CUSTOMIZABLE INTERSTITIAL RADIONUCLIDE BRAIN IMPLANTS, CARRIERS AND METHODS THEREOF". The disclosures of the foregoing applications are hereby incorporated by reference in their entirety.

FIELD

The invention generally relates to using radiation therapy to treat tumors and more specifically to dosimetrically customizable carriers, kits and techniques for using the invention in the treatment of tumors.

BACKGROUND

Tumors in living organisms are highly variable in size, location and their amount of infiltration into normal tissues, the variability of tumors in general make them very difficult to treat with a one-size fits all approach. Furthermore, the extent of tumors and/or void upon debulking are typically not known until presented in the operating room. Thus the options necessary to effectively treat a tumor or tumor bed need to be quite diverse.

Tumors are difficult to eradicate surgically as their infiltrative nature often precludes microscopically complete resection without undue morbidity or mortality. This local persistence of tumor cells may be controlled if sufficient radiation can be delivered safely prior to regrowth and replication of the residual tumor cells. Debulking surgery, followed by radiation therapy in high doses, provides the best chance for local control of a tumor. However, the ability to deliver high doses of radiation in the post-operative setting is frequently limited by intolerance of surrounding healthy tissue. Radiation therapy is divided into external beam radiation therapy (EBRT) or teletherapy and internal radiation therapy or brachytherapy (BT). The therapeutic index is the relative amount of healthy tissue receiving high doses of radiation compared to the dose delivered to the tumor or tumor bed. Improving the therapeutic index may increase local control of tumors and/or decrease the morbidity of treatment. The inherently localized nature of BT is recognized as a technique to improve the therapeutic index in tumor treatment with radiation.

Brachytherapy involves placing a radiation source either into or immediately adjacent to a tumor. It provides an effective treatment of tumors of many body sites. Brachytherapy, as a component of multimodality cancer care, provides cost-effective treatment. Brachytherapy may be intracavitary, as in gynecologic malignancies; intraluminal, as in but not limited to esophageal or lung cancers; external surface, as in but not limited to cancers of the skin, or interstitial, as in but not limited to the treatment of various central nervous system tumors as well as extracranial tumors of the head and neck, lung, soft tissue, gynecologic sites, rectum, liver, prostate, and penis.

The currently available brachytherapy devices and techniques are lacking in the following areas: 1) the current carriers are unable to easily accommodate anatomically conformal and reproducible brachytherapy doses; 2) do not facilitate real-time dosimetric customization for sparing normal tissue, while delivering effective and safe doses of radiation to tumors; and 3) are not able to incorporate additional therapeutic agents, including chemotherapy, and viral, targeted, and DNA damage repair inhibitors.

The present invention addresses the deficiencies associated with current brachytherapy devices for treating highly variable tumors and comprises of novel brachytherapy radioisotope carrier systems and methodology for providing real-time customized brachytherapy treatment to patients with tumors difficult to control using conventional radiation therapy techniques.

SUMMARY

The present invention generally relates to devices, methods and kits for providing a customized radionuclide treatment in a patient to help cure, slow progression or regrowth, or ameliorate symptoms associated with tumors. And more specifically to a versatile dosimetrically customizable brachytherapy system for providing a targeted radionuclide dose to specific tissues on or within the human body.

An embodiment of the present invention comprises a radionuclide carrier system comprising of one or more individual implantable carriers configured to hold radioactive seeds in a precise location relative to a treatment area in order to produce a dosimetrically customizable implant in real-time for an area to be treated and wherein the individual carriers are small enough to fit in or on the area to be treated and the carriers are selected from one or more tile carriers and/or gore carriers. Additional carrier system embodiments may feature only one or more tiles or one or more gores for delivering the radionuclide dose to the tissue of interest.

An additional embodiment of a radionuclide carrier system is the customization and use of a preplanned dosimetry based on precise dimensions and properties of the carriers to optimize the therapeutic index for an affected area. With additional embodiments including precise dimensions and properties of the carriers by utilizing gelatin-based or collaged-based biocompatible materials of differing thicknesses below and/or above a radiation source to act as a spacer to achieve a desired radiation dose delivery and a sparing of normal tissue.

Another additional embodiment achieves the preplanned proper dosimetry by including a layer of tantalum, tungsten, titanium, gold, silver, or alloys of these or other high Z materials as a foil, grid or strip, internal to or on a surface of the carrier to facilitate sparing of normal tissue by diminishing the penetration of the radiation into adjacent normal tissues.

Additional embodiments include carriers manufactured as prefabricated carriers of various shapes and sizes; and some carriers may be preloaded "hot" with the radioactive seeds or "cold" in order to allow the radioactive seeds to be loaded with specifically desired seeds just prior to an implant procedure.

Further embodiments contemplate carriers which may be configured for the use of one or more low-energy radioactive seeds selected from Cs 131, Ir 192, I 125, Pd 103 or other isotopes used intra-operatively following surgical resection to form a permanent implant.

Yet further embodiments may include carriers with short range radioisotopes emitting beta or alpha particles.

Another embodiment of a carrier system comprises carrying additional therapeutic modalities including chemotherapeutic agents, viral treatments, targeted therapies, and/or DNA damage repair inhibitors.

Additional contemplated features of the carriers may include differential color coding to mark end seeds with higher radiation strengths than middle seeds for improved radiation dose distribution for use with limited size and irregularly shaped tumors/tumor beds; arrows, color-coded dots or other visual markers to indicate a proper orientation of carriers in relation to the seeds and treatment areas; indicator lines to allow a user to trim or shape a carrier as needed while maintaining the desired spacing for the calculated dosimetry; and visual and tactile indicators for a user to differentiate the tops from bottoms of carriers in the operating room/operative field and to maintain correct orientation and desired dosimetry.

A further additional embodiment for the carrier system comprises a program/spreadsheet/nomogram to guide a user in the planning of implants and to assist in ordering seeds/carriers based on preoperative shape, lesion size, location, histology and number of seeds needed. Another embodiment comprises a carrier system that is visible on CT and fluoroscopy, and/or is MRI compatible to allow the user to make accurate intra- and post-operative assessments.

An additional embodied radionuclide carrier system is contemplated having at least two individual implantable carriers comprising; at least one tile carrier and one gore carrier; and each carrier is configured to hold radioactive seeds in a precise location relative to a treatment area to produce a dosimetrically customizable implant in real-time for an area to be treated and the individual carriers are small enough to fit in or on the area to be treated. The at least one tile carrier included in the embodied radionuclide carrier system comprises biocompatible materials of differing thicknesses below and/or above a radiation source(s) in order to act as a spacer as well as the use of a layer of tantalum, tungsten, titanium, gold, silver, or alloys of these or other high Z materials as a foil, grid or strip internal to or on the surface of the carrier to facilitate sparing of normal tissue by diminishing the penetration of the radiation into adjacent normal tissues. The at least one gore carrier included in the embodied radionuclide carrier system also comprises biocompatible materials of differing thicknesses below and/or above a radiation source to act as a spacer to achieve a desired radiation dose delivery and sparing of normal tissue. The radionuclide carrier system of the present embodiment is used for intraoperative permanent brachytherapy in treatment of tumors within the central nervous system or its cavities or coverings; and comprises a conformable but dosimetrically stable design for delivery and positioning of radioactive seeds to produce a customizable implant in real-time, piece by piece, for each patient and tumor.

Yet further embodiments of the present invention include inserting the individual implantable radionuclide carriers into or onto a tumor, a void remaining following a tumor resection, or a tumor bed; to help cure, slow progression or regrowth, or ameliorate symptoms associated with the tumor.

Additional embodiments of the radionuclide carrier system is for intraoperative permanent brachytherapy in treatment of various tumors of the body, including but not limited to tumors of the central nervous system, head and neck, soft tissues, bone, spine, lung, breast, skin, esophagus, stomach, liver, intestines, colon, rectum, prostate, pancreas, retroperitoneal space, kidney, bladder, pelvis, ovary, cervix, fallopian tubes, uterus and vagina.

BRIEF DESCRIPTION OF THE DRAWINGS

The principles of the present invention will be apparent with reference to the following drawings, in which like reference numerals denote like components:

FIG. 4 comprises FIGS. 4A and 4B which show two perspective views of alternative shape designs for tile carriers.

FIG. 5 represents a drawing in which embodied individual tiles are shown in use in a post-operative cavity after tumor debulking.

FIG. 12 comprises FIGS. 12A and 12B wherein

FIG. 13 comprises FIGS. 13A, 13B and FIG. 13C wherein

DETAILED DESCRIPTION

Definitions

Figure 1:
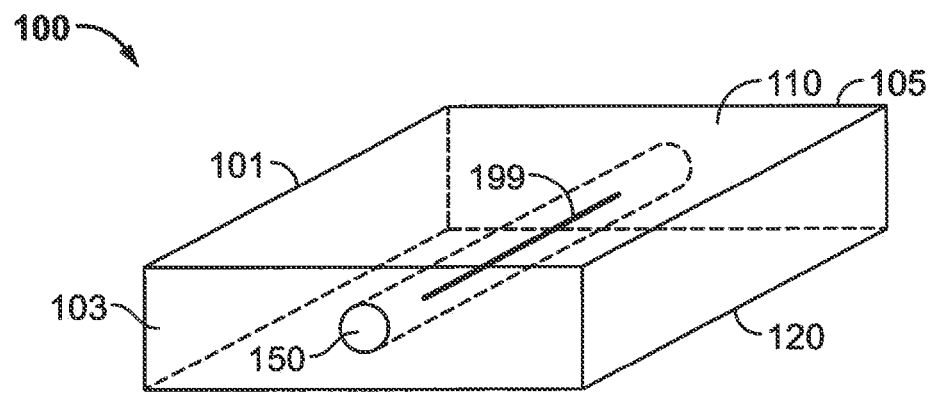
FIG. 1 shows a perspective view of an embodied carrier device in a tile form.

For the purposes of the present invention Brachytherapy is defined as radiation treatment in which the source of the radiation is placed close to the surface of the body or within the body or a body cavity a short distance from the area being treated.

For the purposes of the present invention Teletherapy is defined as radiation treatment in which the source of the radiation is at a distance from the body.

For the purposes of the present invention High Dose Rate is considered to be defined as the treatment with radiation doses above 12,000 cGy/hr.

For the purposes of the present invention Low Dose Rate is considered to be defined as the treatment with radiation in the dose range of 400-2000 cGy/hr For the purposes of the present invention High Z Materials are considered to be defined as any element with an atomic number greater than 20, or an alloy containing such materials.

For the purposes of the present invention the term Hot is considered to be a material that is Radioactive and the term Cold is considered to mean a material is low in radioactivity; or not radioactive.

For the purposes of the present invention Dosimetry is defined as the process of measurement and quantitative description of the radiation absorbed dose (rad) in a tissue or organ.

For the purposes of the present invention a Tile Carrier sometimes also referred to as a GammaTile is defined as a type of radionuclide carrier that is planar and maintains a two-dimensional planar geometry when placed in use to treat tumors.

For the purposes of the present invention a Gore Carrier sometimes also referred to as a GammaGore is defined as a type of radionuclide carrier that, while initially planar, will assume a 3-dimensional shape when arranged and placed into an operative cavity or similar space and conform to the treatment environment while maintaining the geometry necessary for an effective implant.

For the purposes of the present invention the term Interstitial is defined as pertaining to parts or interspaces of a tissue.

For the purposes of the present invention the term Tumor: is defined as an abnormal growth of tissue resulting from uncontrolled, progressive multiplication of cells; which can be benign or malignant.

For the purposes of the present invention the term Malignant is defined as tumors having the potential for or exhibiting the properties of anaplasia, invasiveness, and metastasis.

For the purposes of the present invention the term Cancer is defined as any malignant, cellular tumor.

For the purposes of the present invention the term Chemotherapy is defined as a cancer treatment method that uses chemical agents to inhibit or kill cancer cells.

Application of Embodied Carriers in Central Nervous System Tumors

Despite meticulous surgical technique, tumors metastatic to the brain or spine often recur at or near the site of resection. This is because it is rarely feasible to resect these tumors with pathologically negative margins, especially in the more eloquent regions or where lesions are adjacent to vascular structures or nerves. Radiation therapy, utilizing an increasingly large variety of techniques, has been shown to be the single most effective adjuvant treatment to help prevent recurrence of malignant brain tumors. Interstitial brachytherapy combined with surgical resection of central nervous system tumors has been in use for several decades. Various types of radioactive sources are inserted under direct visualization during the surgery, as potentially more cost effective and less time-consuming therapy, without compromising outcomes.

Nevertheless, techniques for interstitial brachytherapy (BT) of central nervous system tumors have remained relatively crude. The brachytherapy device and methods embodied in the present invention improve the delivery of radiation by creating a carrier system to create combinations of carriers (tiles and/or gores) each with radioactive sources contained within. These carriers, known as tile carriers or "GammaTiles" (GT's) and gore carriers or "GammaGores" (GG's) can be positioned to fit into operative beds by customizing them to the shape and size of individual operative cavities. The GTs can be tailored to protect sensitive normal structures, such as nerves or normal brain, while delivering desired high doses of radiation to the precise locations at highest risk of recurrence. The GTs may also be used as carriers for short-range radioisotopes emitting beta or alpha particles or for delivery of other therapeutic modalities, including chemotherapeutic agents, viral treatments, targeted therapies, and/or DNA damage repair inhibitors. They may also be designed to contain high Z materials and/or biocompatible spacers to afford significant directionality to the radiation treatment.

Application of Embodied Carriers Outside the Central Nervous System

Brachytherapy has been used to treat many tumors of extracranial sites such as head and neck, lung, soft tissue, gynecologic, rectum, prostate, penis, esophagus, pancreas and skin. Brachytherapy (BT) can be used alone or in combination with external beam radiotherapy and/or surgery. Patient outcomes are critically dependent upon proper patient selection and implantation technique. In general, patients with tumors that are intimately associated with critical normal structures to be preserved such as nerves, vessels, cosmetically apparent areas or visceral organs cannot be completely resected without undue morbidity or mortality. These tumors may be good candidates for BT performed in conjunction with surgical resection. Currently available techniques to produce the reliable source spacing needed for optimal geometry and subsequently radiation dosimetry, require catheters and shielding that are relatively bulky and therefore poorly conforming to the treated area. Consequently, they require considerable capital investment and the presence of a team of experts for effective use; and when preformed intraoperatively must be undertaken in a specially shielded operating room to avoid irradiation of adjacent staff and patients. These shortcomings limit the availability of these therapies to very few centers and compromise outcomes by decreasing tumor control and increasing complications from therapy. The brachytherapy device and methods contemplated in the present invention facilitates achieving optimal radioactive source arrangements for permanent low dose rate (LDR) BT in a user-friendly, readily available and cost-effective manner, by using a carrier system of geometrically customizable carriers (GTs/GGs) to contain radioactive sources to be placed into tumors or tumor beds.

Furthermore, the embodiments of the present invention also enables users to preferentially spare sensitive normal tissue without compromising the ability to deliver high dose radiation customized to both tumor and patient anatomy.

Additional embodiments of the tile and/or gore carriers may include the ability of the tile and/or gore carriers to deliver other cytotoxic agents, such as chemotherapy drugs or very short range radioactive sources such as Y-90 and alpha particles for placement directly into tumors, while maximally sparing normal tissue.

Illustrative embodiments of the invention are described below. In the interest of brevity, not all features of an actual implementation are described in this specification. It will, of course, be appreciated that in the development of any such actual embodiment, numerous implementation-specific decisions such as compliance with regulatory, system-related, and business-related constraints, which will vary from one implementation to another, must be made to achieve the specific goals. Moreover, such a developmental effort might be complex and time-consuming but with the benefit of this disclosure, would be a routine undertaking for those skilled in the art of radiation therapy.

Carrier Systems

Generally the carrier systems described herein and exemplified in FIGS. 1-11 involve the utilization of small individual implantable carriers in the form of tiles (as shown in FIGS. 1-6) and gores (as shown in FIGS. 7-11) designed to be bearers of therapeutic agents such as radioactive seeds to produce a dosimetrically customizable implant in real time for each patient and lesion.

The carrier systems are designed to: create a carrier which allows for more precise and predictable dosimetry; an improved geometry with a better orientation of seeds to one another especially in the settings of real-time, intraoperative environments; is fully customizable to adjust to size/volume, location, and tumor type; and can provide differential dosing of tumor/tumor bed vs. normal tissues.

The carrier systems embodied are generally made of biocompatible materials known in the art and more specifically may be made of gelatin based or collagen based biocompatible materials.

EXAMPLE 1

Tile Carrier Embodiment

FIGS. 1-6 show various exemplifications of carrier devices in tile form embodied in the present invention.

FIG. 1 shows a perspective view of an embodied carrier device 100 in a tile form wherein the tile 101 serves as a loadable shieldable spacer for a radioactive seed 199 and wherein the embodied tile 101 comprises a pre-formed loading channel 150 which runs from a proximal end 103 through to a distal end 105. Additionally there is an antipodal surface 110 opposite of the treatment surface 120. The approximate dimensions contemplated of a tile as shown here would be a square with each side about 1 cm and the depth of the device as measured as the distance from the antipodal surface 110 to the treatment surface 120 may be about 2-7 mm, with 3-6 mm preferred, 4-5 mm more preferred, and 4 mm most preferred. A loading channel 150 may be preformed as shown or created at time of radioactive seed 199 placement. The seed 199 will generally be placed in the center of the loading channel 150 and there are various ways to insure proper placement of the seed 199 within the channel. Furthermore the antipodal surface 110 may additionally comprise various colored markers, indicators and textural features which may further insure proper orientation of the tiles 101 when being placed.

Figure 2:
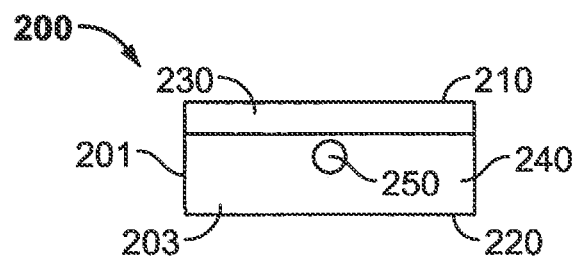
FIG. 2 shows a front plan view of another embodied carrier device in a tile form.

FIG. 2 shows a proximal 203 or end view of another embodied tile form carrier 201 and demonstrates the positioning of the loading channel 250 in respect to the tile 201. In this example the loading channel 250 itself may be offset within the tile 201 such that the channel 250 is located closer to either the antipodal 210 or the treatment 220 surface depending on the exposure wanted and/or the shielding constraints desired with the radionuclide seed 199 (not shown) within the loading channel 250. In the case shown there is a thin layer of material 230 on the antipodal side 210 and a thicker layer 240 in which the loading channel 250 is formed.

Figure 3:
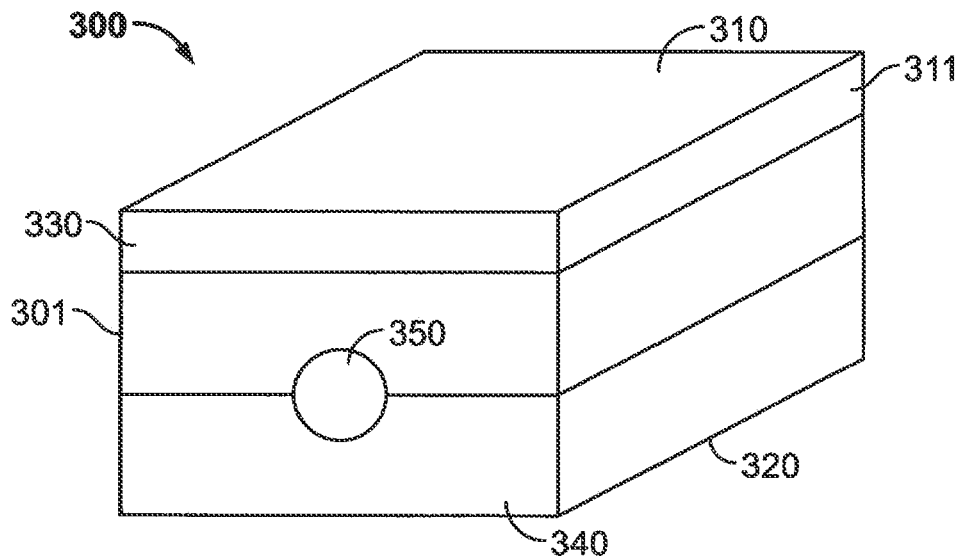
FIG. 3. Comprises a perspective view of another embodied carrier device in tile form wherein the tile further includes a metal foil at the antipodal surface distal to the treatment zone.

FIG. 3 shows a perspective view of another embodied tile 301 wherein the tile further includes a metal foil 311 on the antipodal surface 310. One or more surfaces can include a metal foil layer 311 on the antipodal surface 310 such as gold to block rads from escaping and/or redirect them or focus them towards the target treatment area. Some of the metals contemplated for use include a layer of tantalum, tungsten, titanium, gold, silver, or alloys of these or other high Z materials on the antipodal aspect (additionally the metal layers may be located internally between spacing layers in either GammaTile or GammaGores not presently shown) to provide sparing of normal tissue in portions of brain and elsewhere where there is very limited physical space. Additionally, the embodied tile 301 may include a loading channel 350 which may be located between an upper spacer layer 330 which may the thicker portion located away from the treatment surface 320 and a lower spacer 340 which is the thinner portion located adjacent to the treatment surface 320.

The present invention contemplates of carrier construction using differential thicknesses of biocompatible materials below and/or above the radiation sources (as shown in FIG. 3 above) to achieve differential radiation dose delivery with relative sparing of normal tissue along with the use of a layer of tantalum, tungsten, titanium, gold, silver, or alloys of these or other high Z materials on the antipodal aspect (side away from the tumor) or internal to the Tiles or Gores to provide sparing of normal tissue in portions of the body such as the brain and anywhere there is very limited physical space.

FIG. 4 shows a perspective view of two alternative tile shapes including a circular tile 401 and a square tile 501 in any given tile contemplated in the present invention the loading channel 450, 550 may be preformed or may be marked for loading with a sharp instrument such as a needle, or may be blank and the channel may be formed wherever the user determines makes the most sense from a dosimetry, geometry and/or orientation standpoint.

FIG. 5 represents a drawing in which embodied individual tiles 501 are shown in use in a post-operative cavity after tumor debulking. In this case four individual or interconnected tiles 501 are placed within the cavity adjacent to the tissue margins where the debulking occurred wherein the radionuclide seeds 599 target the tissue around the lesion margin and the tile 501 shields the other tissues and void space from the radionuclide exposure. The treatment surface 520 lies closest to the tumor bed and the antipodal surface 510 faces the void space. Further embodiments contemplated but not shown include the use of notches, matched tongue and groove, slot/groove, key lock, lego-block or similar mating/matching type systems to secure and fit the tiles 501 next to each other to provide optimal geometry and orientation and increase the customization to a broad realm of effective treatment possibilities.

Figure 6:
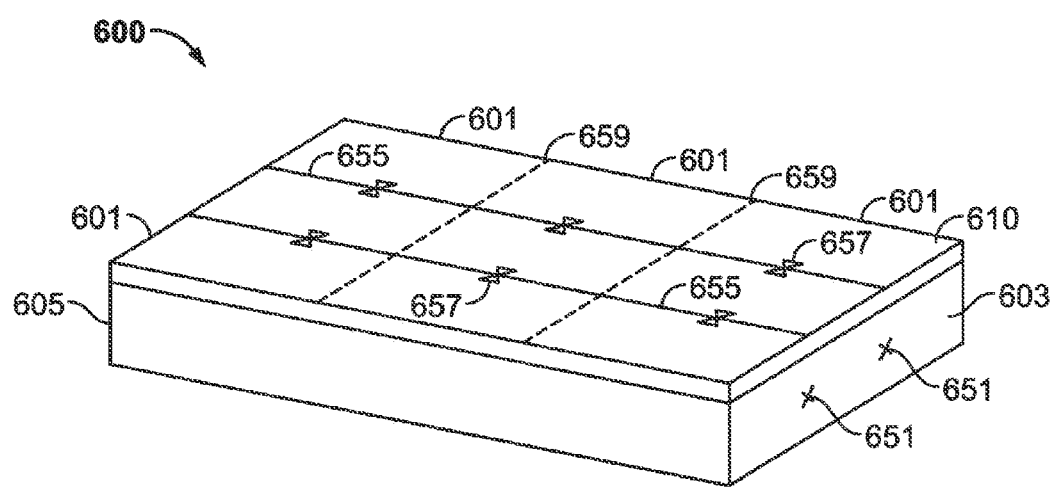
FIG. 6 shows a perspective view of another contemplated carrier system in tile form.

FIG. 6 shows a perspective view of another contemplated carrier system 600 in tile 601 form. The tile sheet shown 601 includes three equal size tiles. The carrier system 600 is marked with indicator lines 659, which would allow users to trim/shape tiles 601 to the needed size but still maintain desired spacing for the dosimetry. The use of tiles 601 of certain precise dimensions allow for the carrier to guide the user to maintain the precise and preplanned dosimetry needed to produce effective and safe outcomes. For example a contemplated device may be 1.0 cm on center spacing between seeds in tile, and 0.5 cm spacing to tile edge. So the next tile, if added, maintains overall 1.0 cm spacing pattern and the preprinted "cut here" lines 659 shown may be 0.5 cm between each seed so a 2×3 linear carrier could be size-trimmed to a 2×2 tile or 2×1 tile in the operating room. Additionally, the antipodal surface 610 of FIG. 6 includes a top differentiator with the markings 659 and 657 provided. In this case there are trim lines loading channel orientation lines 655, seed location markings 657 and trim lines 659. Additional concepts for differentiating the tops (antipodal surface 610) from bottoms (treatment surface 620) of the carriers in the operating room/operative field; can utilize color, texture, glossy/dull, etc, to maintain correct orientation, and therefore, optimal dosimetry. Additionally, both ends 603 and 605 of the tile or just the proximal end 603 may be marked with loading channel placement guides 651 for tiles 601 fully customizable and not including a preformed loading channel 650 (not present in this tile).

The present carriers may include the use of differential color codes to mark end seeds with higher radiation strength than the middle seeds for improved radiation dose distribution for use with limited size and irregular shape targets.

Additional carriers may include the use of markers (color coded dots, arrows, etc) to indicate proper orientation of the tiles. For example, as seeds have both a long and short axis that may not be readily apparent once in the tile, and tiles may be square, or adjacent to other tiles, "green arrow to green arrow, red arrow to red arrow" could indicate both correct seed orientation, and give another guide to precise line-up during placement.

The carriers may be manufactured in multiple size and shape prefabricated tiles of various shapes and sizes (e.g., 1×1 cm, 2×2 cm, 1×3 cm, 2×3 cm, 1×4 cm); these may be preloaded (hot) with the radioactive seeds, or cold to allow for the radioactive seeds to be placed within the tumor or bed just prior to the procedure, which simplifies manufacture of tile for greater variety of carriers, reduces the waste of unused "hot" carriers, and reduces the radiation exposure of the staff.

Additional carriers may also have an impermeable membrane, bio-compound, high Z material or other barrier, which acts to prevent or impede the migration of the compound(s) or agents from the side(s) of the carrier(s) adjacent to the resected tumor to the antipodal side(s) of the carrier(s) (adjacent to normal tissue) and vice versa to create a differential therapeutic impact on the operative bed vs. adjacent tissues.

Additional carriers may use differential thickness of tissue equivalent material below and/or above the tiles and/or a construction of differing high z materials (or just the seed "tube" built into the tile) to achieve the desired radiation dose delivery or normal tissue sparing targeting.

EXAMPLE 2

Gore Style Carriers

FIGS. 7-11 show various exemplifications of carrier devices in gore form embodied in the present invention.

One problem associated surgeons and oncologists often face when treating a subject include a subject with spherical and semispherical intracranial lesions which are common and thus so are similarly shaped postoperative cavities. Any useful carrier and coverage will need to adapt to this shape while being able to be implanted into the brain, and still maintain "ideal" or nearly ideal geometry. One solution embodied by the present invention includes the creation of two-dimensional gores that act as carriers, and when loaded with seeds and placed in the cavity conform to the three-dimensional environment while maintaining geometry of implant. In addition to the three-dimensional nature of the carrier, the carrier may possess additional possible properties previously mentioned including spacing function, differential thickness, and the possibility of combining with high-z materials for radiation protection. These carriers may also be designed so as to be compatible with placement of adjacent tiles or gammatiles as needed for additional intraoperative flexibility.

Additionally the gore-type carrier may be pre-manufactured in specific dimensions and available in a variety of sizes and/or capable of being trimmed to make smaller or combined to make bigger at time of use. The dimensions decided upon can be customized by the user based upon the tumor/cavity size and characteristics to achieve the necessary geometry.

Although certain design shapes are shown as exemplary products in FIGS. 7-11, other geometric shapes such as regular or irregular polyhedrons also may be used as gore-style carriers.

Figure 7A:
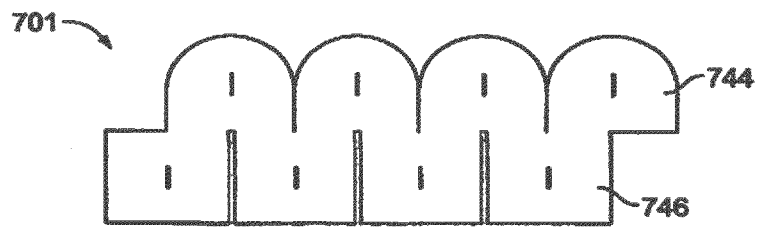
FIG. 7 comprises FIGS. 7A, 7B, and 7C which are front plan views of three embodied carrier systems in gore form and in a 2-dimensional form.
Figure 7B:
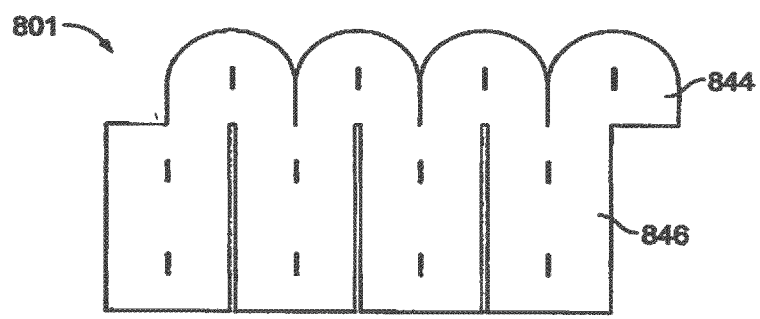
Figure 7C:
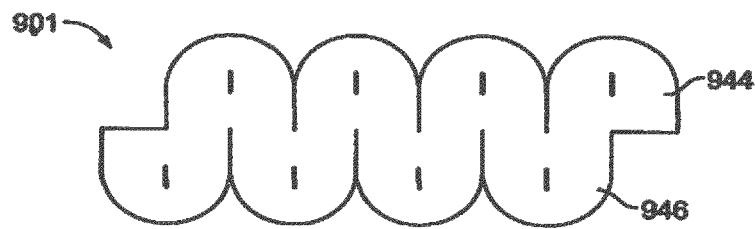

FIG. 7 comprises FIGS. 7A, 7B, and 7C which are front plan views of three embodied carrier systems in gore form and in a 2-dimensional form. The general gore designs include petals, flaps, and/or a combination of petals and flaps. FIG. 7A shows a 2 dimensional gore design 701 with comprising petals 744 and flaps 746. FIG. 7B shows a gore 801 with petals 844 and flap 846 but in the design the flaps have an extended length to provide for a different geometrical or size application. FIG. 7C shows a gore 901 with a Bi-concave design with double petals 944.

Figure 8A:
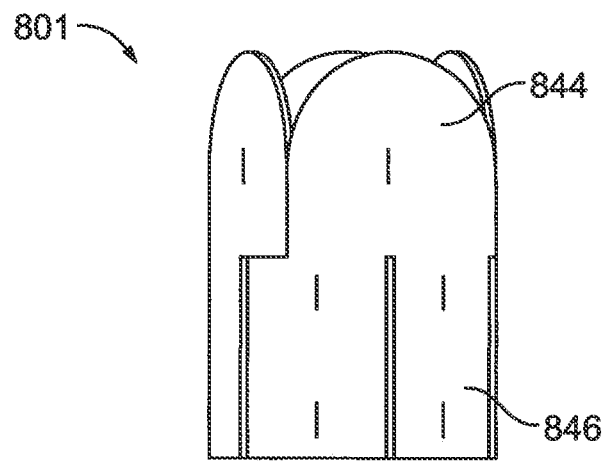
FIG. 8 comprises FIGS. 8A and 8B which are front plan views of the gore carrier shown from 7B when in 3-dimensional forms.
Figure 8B:
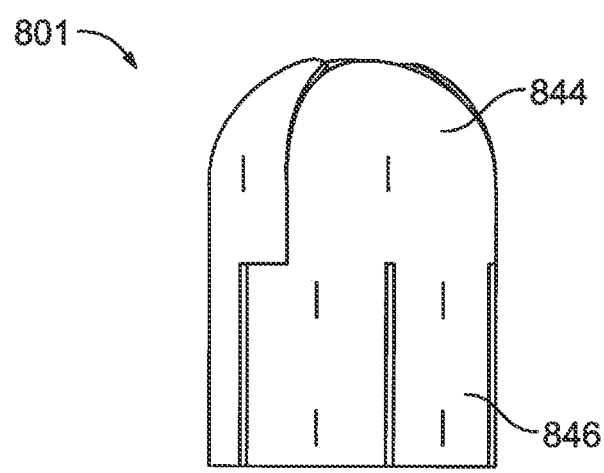

FIG. 8 shows FIGS. 8A and 8B which are front plan views of the gore carrier 801 shown 7B when in 3-dimensional forms. FIG. 8A shows the gore 801 rolled up to cover a 3-dimensional space which in more cylindrical and FIG. 8B shows the gore 801 rolled up with the petals 844 folded inward which creates a closed cylinder with a rounded top 3-dimensional conformation.

The proportions are generally fixed by height, width and length, and set by need to maintain ideal implant geometry of seed spacing. The exact length and width depends upon the cavity size but the gore carrier itself may be pre made and/or pre-sized. The gore-type carrier additionally may have seed location presets.

Figure 9A:
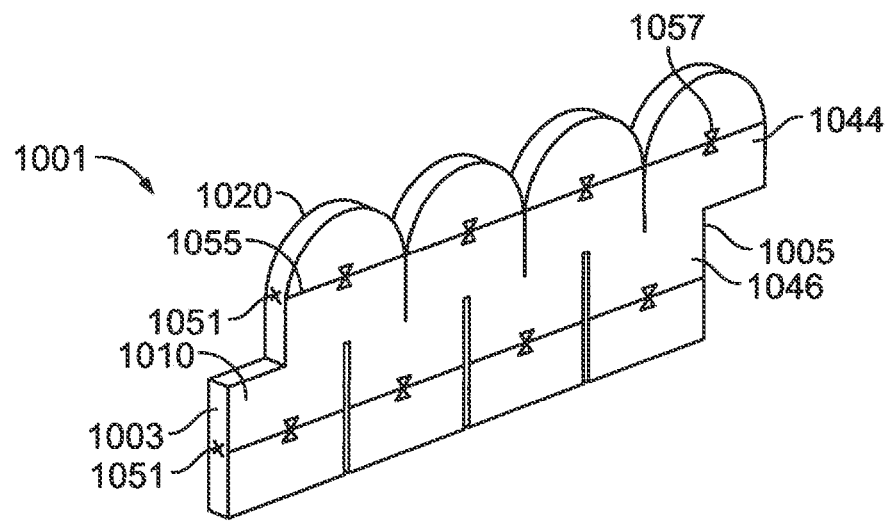
FIG. 9 comprises FIGS. 9A and 9B which are perspective views of more embodied gore carriers in different shapes.
Figure 9B:
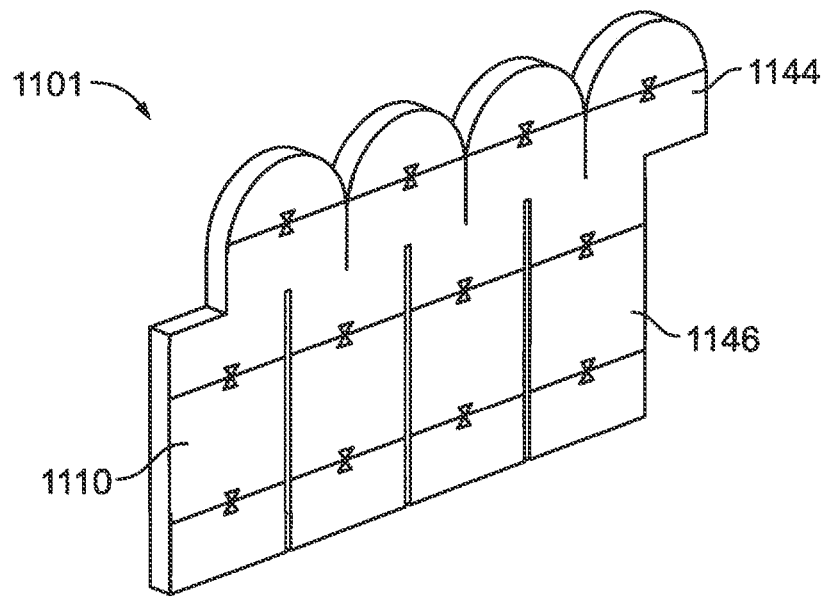

FIG. 9 includes FIG. 9A which shows a 2-dimensional gore designs 1001, with petals 1044, and flaps 1046. The antipodal surface 1010 is viewable and the treatment surface 1020 is hidden. The gore 1001 further includes marking identifiers on the antipodal surface 1010 including loading channel orientation lines 1055 and seed location markings 1057. Additionally, both ends 1003 and 1005 of the gore or just the proximal end 1003 may be marked with loading channel placement guides 1051. FIG. 9B shows a gore 1101 with petals 1144 and flap 1146 but in this design the flaps have an extended length to provide for a different geometrical or size application. For example, the extended length flaps may provide a better fit in a larger cavity. In both FIGS. 9A and 9B the gore is rolled inward and the antipodal sides 1010 and 1110 respectively are not viewable once the gore is placed in its rolled up 3-dimensional configuration.

Figure 10A:
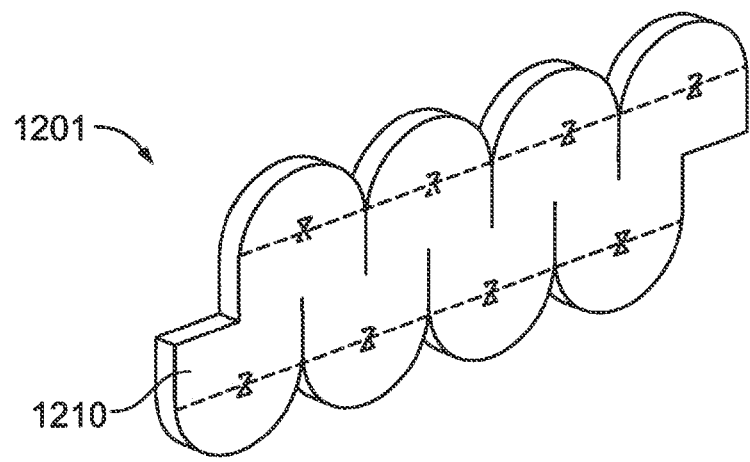
FIG. 10 comprises FIGS. 10A and 10B which represents two views of an embodied carrier in gore form.
Figure 10B:
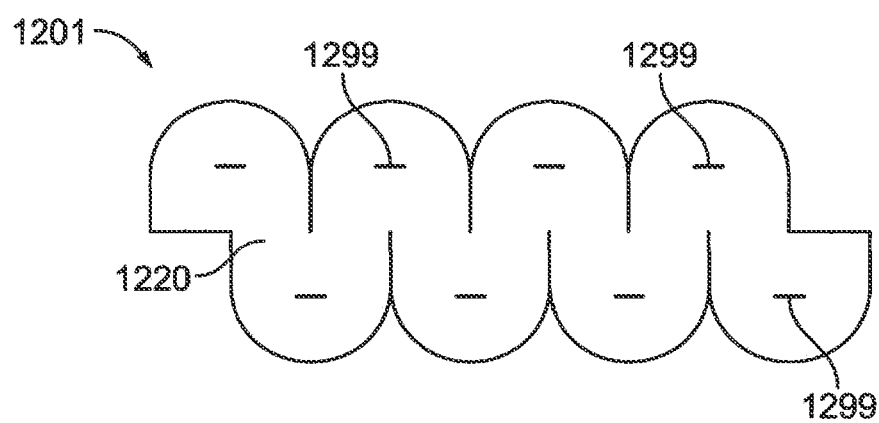

FIGS. 10A and 10B show another embodied gore 1201 wherein FIG. 10A shows a perspective view with the antipodal surface 1210 viewable and FIG. 10B is a plan view of the treatment surface 1220 which shows the seed 1299 distribution within the gore 1201. The gore is designed to roll up and the treatment surface 1220 faces the tumor or treatment bed and the antipodal surface 1210 faces the interior of the 3-dimensional sphere-like gore. This bi-concave design with double petals, may best be used in more spherical type cavities.

Figure 11:
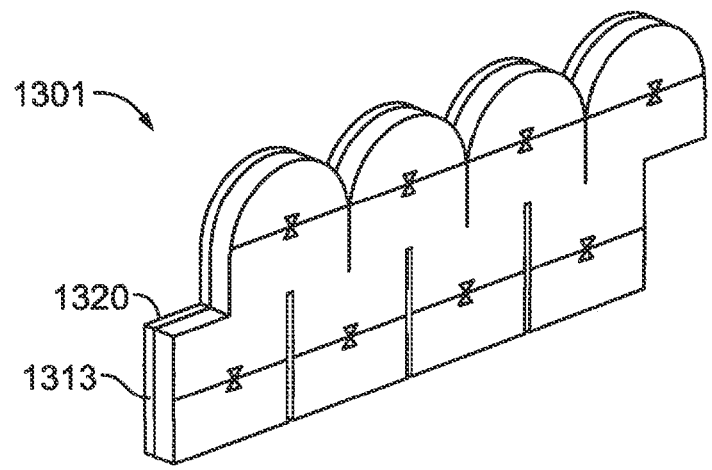
FIG. 11 shows a perspective view of another embodied carrier in gore form.

FIG. 11 shows a perspective view of another embodied carrier in gore 1301 form wherein the treatment surface 1320 includes an additional layer 1313 which may be used to provide for a localized delivery of radioactive materials such as gamma or beta irradiation or alpha particles along with chemotherapy agents or tumoricidal/targeted/immunotherapeutic or viral/viral vector agent(s) on the side(s) of the carrier(s) adjacent to the tumor.

The carriers of the present invention may also provide for the use of a small implantable individual carrier constructed for the localized delivery of radioactive materials such as gamma or beta irradiation or alpha particles along with radiation sensitizing agents and/or radiation damage repair inhibitors on the side(s) of the carrier(s) adjacent to the tumor.

The carriers of the present invention may also provide for the use of a small implantable individual carrier constructed for the localized delivery of radioactive materials such as gamma or beta irradiation or alpha particles with or without other radiation protection compounds on the side(s) of the carrier(s) antipodal to the radiation source and/or tissue growth promotion/healing factor compounds on the side(s) of the carrier(s) antipodal to the radiation source.

The general gore designs include petals, flaps, and/or a combination of petals and flaps. The proportions are generally fixed by height, width and length, and set by need to maintain ideal implant geometry of seed spacing. The exact length and width depends upon the cavity size but the gore carrier itself may be pre made and/or pre-sized. The gore-type carrier additionally may have seed location presets. When the gore-type material is similar to the petal flap system found in FIG. 9A the petals and flaps offset to maintain seed spacing. The seed spacing contemplated may range from 0.5 cm to 1.5 cm, with 0.75 cm to 1.25 cm preferred, 0.8 cm to 1.2 cm more preferred and 1.0 cm a most preferred seed spacing interval between seeds.

The present invention also may include the use of a small implantable individual carrier constructed for the localized delivery of radioactive materials such as gamma or beta irradiation or alpha particles along with chemotherapy agents or tumoricidal/targeted/immunotherapeutic or viral/viral vector agent(s) on the side(s) of the carrier(s) adjacent to the tumor.

The present invention also may include the use of a small implantable individual carrier constructed for the localized delivery of radioactive materials such as gamma or beta irradiation or alpha particles along with radiation sensitizing agents and/or radiation damage repair inhibitors on the side(s) of the carrier(s) adjacent to the tumor.

The present invention also may include the use of a small implantable individual carrier constructed for the localized delivery of radioactive materials such as gamma or beta irradiation or alpha particles along with radiation protection compounds on the side(s) of the carrier(s) antipodal to the radiation source and/or tissue growth promotion/healing factor compounds on the side(s) of the carrier(s) antipodal to the radiation source.

The tiles and/or gores in the present invention include the adaptability of the carrier system to be isotope specific and manage the radionuclide strength and exposure to users and normal (non-targeted) tissues with a variety of measures including differential thicknesses as shown above, seed-tubes (not shown), shielding materials, or spacing facilitators to place radiolabeled seeds in best place in regards to treatment of target and non-treatment of non-target.

The carriers may be MRI compatible and/or visible on fluoroscopy and CT to facilitate accurate intra- and post-operative assessment.

The small individual implantable tiles and/or gores are designed to be carriers for radioactive seeds used to produce a dosimetrically customizable implant in real time for each patient and tumor.

Radionuclide Seed Loading

Figure 12A:
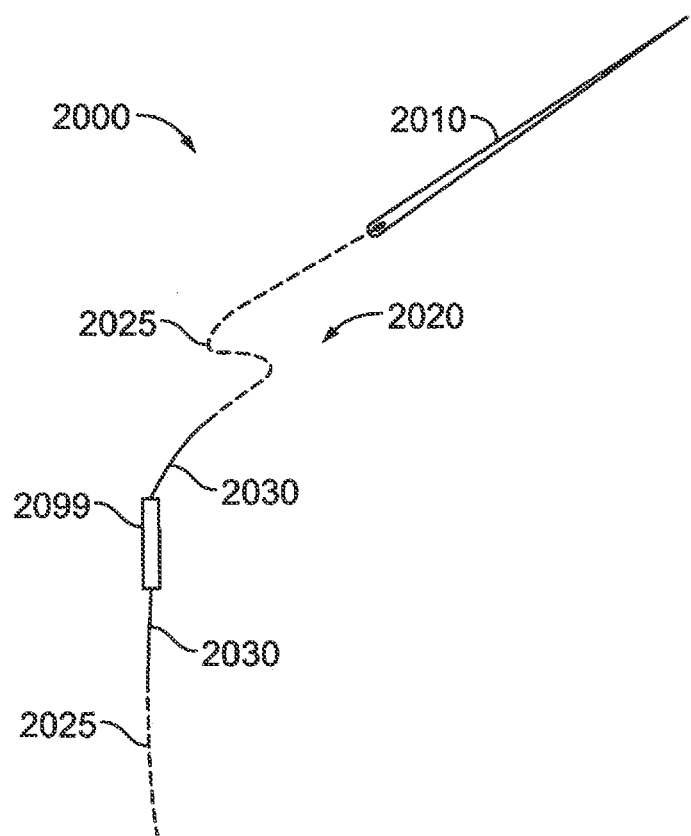
FIG. 12A shows an embodied needle radionuclide seed loading device contemplated and FIG. 12B shows a perspective view of a carrier device with proper radionuclide seed placement.
Figure 12B:
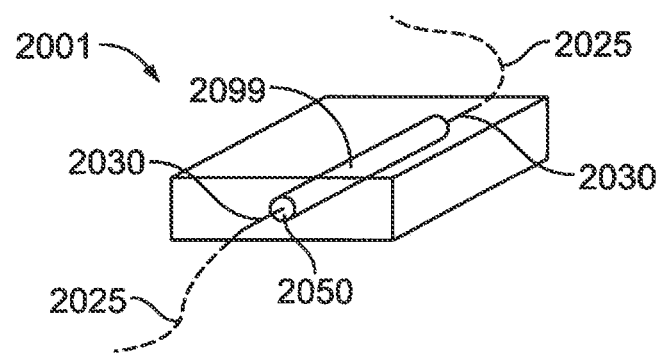

FIG. 12A demonstrates the use of a loading needle apparatus 2000 contemplated in the present invention. The apparatus 2000 comprises a needle 2010 attached to a specific vicryl thread 2020 and at least one radionuclide seed 2099 in a strand depending on the carrier and conditions to be loaded. The vicryl thread 2020 comprises a regular color section of thread 2025 and an offset color portion of thread 2030. When the offset color portion of thread 2030 is visible out of either end of a gore carrier, tile carrier or carrier loader the visual presence is indicative that the seed is not placed in its proper location. FIG. 12B exemplifies the use of a needle apparatus 2000, the needle apparatus is used to penetrate the tile carrier 2001 and create a loading channel 2050 through the tile 2001. When the seed is placed at the proper depth all of the offset color 2030 (such as purple) vicryl disappears inside of the tile device and the regular color thread 2025 is trimmed away.

The present invention may use a variation of seeds in any carrier in order to provide the best dosimetry for the patient tumor and space. Additionally, the loading strands may include one or more of the same seeds or various combinations of well-known low energy radioactive seeds such as Cs 131, Ir 192, I 125, Pd 103 or others commonly known in the art. The seeds placed within the carriers are generally placed as a therapeutic agent in the form of permanent implants intra-operatively following surgical resection, but there may be instance where implants are interchanged removed or replaced.

In other possible loading carriers (Not shown) the carrier may include an "up" or "top" designation on the side opposite of the target zone surface. The hot seed may be encased in a plastic cartridge and loaded into the device with a colored vicryl or similar thread, such that when the seed is loaded into the appropriate position within the tile only certain thread colors are visible, once the alignment is complete the strings on both sides may be pulled, thus pulling the two halves of the plastic cartridge shielding the hot seed. And thus allowing the unshielded hot seed to reside in its proper position within the tile device.

Loading Devices

The present invention also includes a specialized loading device designed to enable the medical team to create a carrier for each patient and tumor reliably, reproducibly and efficiently.

Figure 13A:
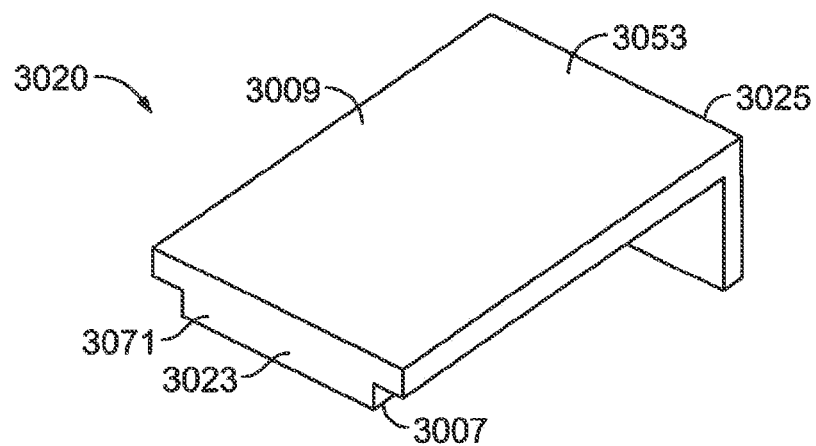
FIG. 13A shows a perspective view of a lid to an embodied loading device.
Figure 13B:
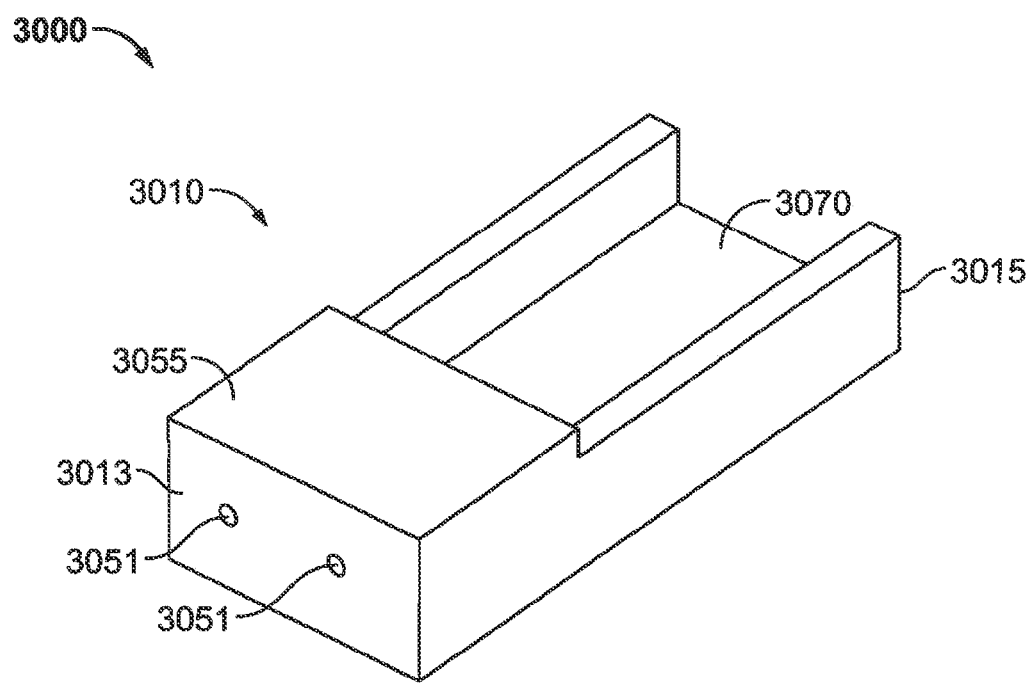
FIG. 13B shows a perspective view of the base of an embodied loading device.
Figure 13C:
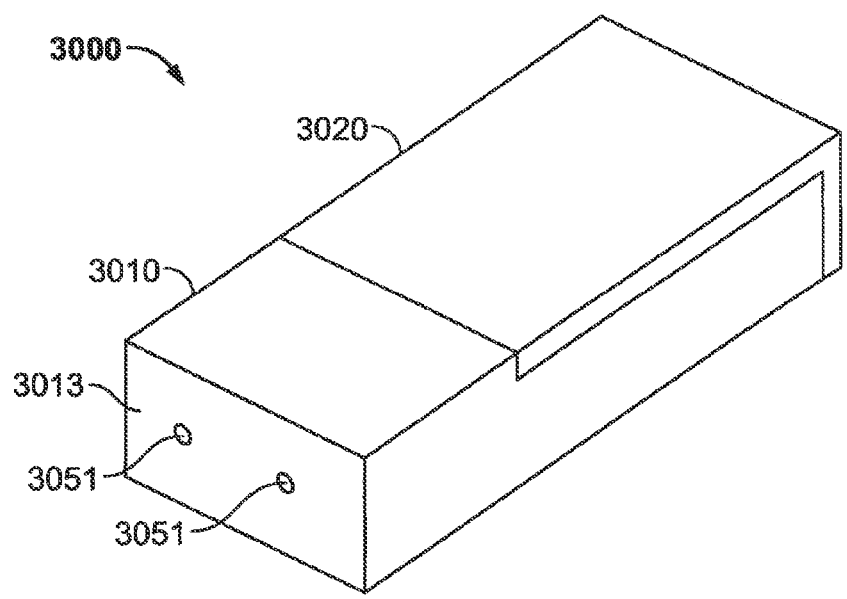
FIG. 13C shows a perspective view of and an embodied loading device with the lid in its secured position on the base.
Figure 14:
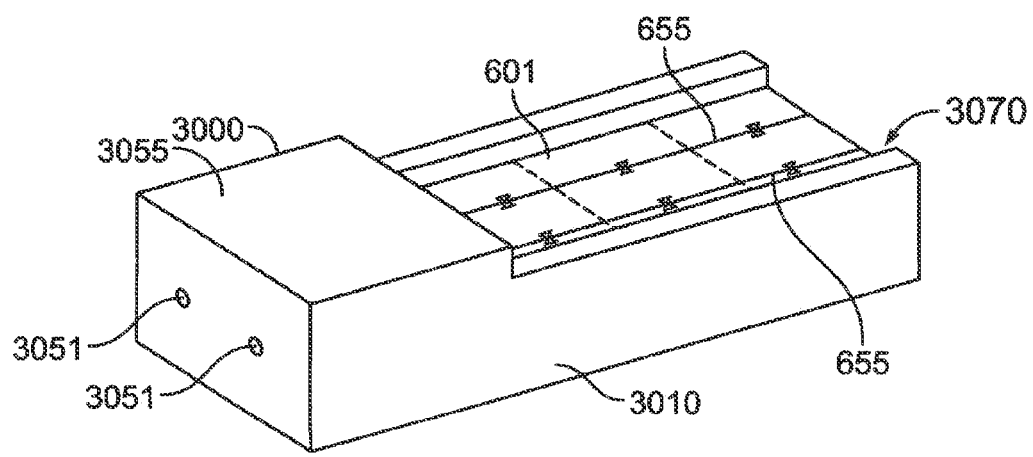
FIG. 14 is a perspective view of an embodied carrier in tile form placed in a loading device for enhanced radionuclide loading capabilities.
Figure 15:
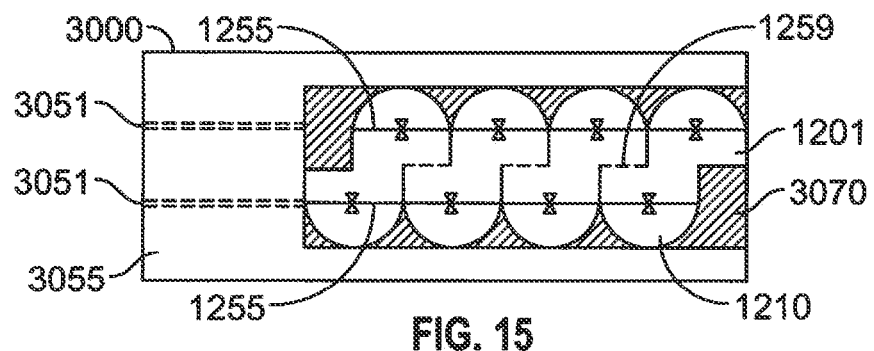
FIG. 15 is a top plan view of an embodied carrier in gore form placed in a loading device for enhanced radionuclide loading capabilities.

FIGS. 13-15 demonstrate the use of a specialized loader system for loading the carriers of the present invention with radioactive seeds. The loaders of the present invention may be used with the carriers either to create prepackaged hot carriers or to load "cold" carriers just prior to use.

The embodied loaders can be single or multi-use, sterilizable, and shielded if desired. They are designed to load either standard or high-Z material carriers in an accurate, efficient, and real-time manner. The loaders are of similar designs, dimensionally specific, and each consists of two components, the base and the lid.

The base of the loaders functions to: 1) guide the initial path of the loading needle for seed placement in the carrier; 2) provide dimensional stability to the soft carrier during the loading process; 3) center the carrier left-right within the base during the loading process; and 4) shield the user.

The lid of a contemplated loader function to: 1) guide the final path of the loading needle, entirely through the carrier; 2) provide dimensional stability to the soft carrier during the loading process; 3) position the carrier superior-inferiorly within the base during the loading process; 4) position the carrier front to back within the base during the loading process; and 5) shield the user.

The loader designs of the present invention can be made to accommodate a wide variety of GammaTile and GammaGore dimensions and styles. They are illustrated to accommodate seed-in-suture, but can be easily adapted for loose seeds or other configurations.

When loading a seed in suture a needle longer than the loader is used and pulled through the loader channel holes on the proximal end of the base and the distal of the lid. Once the needle protrudes it is pulled the rest of the way with clamps or a needle-nose plier. For example, if the user uses a 60 mm loader the user would want to use a 70 mm needle to feed through the loader channels and deposit the seeds within the carrier.

FIG. 13 includes FIGS. 13A and 13B wherein FIG. 13A shows a perspective view of a lid 3020 to an embodied loading device 3000. FIG. 13B shows a perspective view of the base 3010 of an embodied loading device 3000. And FIG. 13C shows a perspective view of an embodied loading device 3000 with the lid 3020 in its secured position on the base 3010. The lid 3020 has a bottom surface 3007 and a top surface 3009, a proximal end 3023 and a distal end 3025, and a loading bed insert 3071 located on the bottom surface 3007 and running from the proximal end 3023 to the distal end 3025. Additionally there are loading channel 3053 exit holes (not shown) extending through the distal end 3025 of the lid. The base 3010 as shown in FIG. 13B comprises of the proximal end 3013 and a distal end 3015, a proximal end loading channel 3051 and a loading channel support structure 3055, which provides enough depth to guide a needle in a consistent and accurate pathway as the needle tip travels through any loading material if present, and exits out a loading channel exit hole 3053. Additionally the loader 3000 comprises a loading bed 3070 in which appropriately sized carrier material is placed to be loaded. Once a carrier is placed into the loading bed 3070 to be loaded, the lid 3020 is placed onto the base 3010 such that the loading bed insert 3071 located on the bottom surface 3007 of the lid 3020 engages with the loading bed 3070 portion of the base 3010. The depth of the loading bed insert 3071 is chosen so that it is deep enough to sandwich and the carrier material in place during the process of loading, but not too much depth which crushes the carrier, and repulses the ability of the loading needle to extend through a loading channel 3050.

FIG. 14 is a perspective view of the embodied tile carrier 601 previously shown in FIG. 6 when placed in the loading bed 3070 of the loading device 3000 of FIG. 13. FIG. 14 shows the tile 601 is placed within the loading bed 3070 portion of the loader 3000. The lid 3020 portion of the loader has been removed so that the tile 601 is visible and one can see that the orientation lines 655 of the tile 601 align directly with the proximal end loading channel 3051 such that when a needle loader enters through the proximal end loading channel 3051 and extends through the loading channel support structure 3055 and enters into the loading bed portion 3070 of the base 3010 where a carrier tile 601 is in a secured position; the loading needle enters into the predetermined placement on the tile 601 based on dosimetry needs for treatment. And if the lid 3020 were present, the needle would extend through the loading channel exit hole 3053 and exit out of the device leaving the loaded carrier 601 behind.

When the needle loading apparatus is one such as that described in FIG. 12A, the needle apparatus 2000 feeds through the proximal end loading channel 3051 and extends through the loading channel support structure 3055 and enters into the loading bed portion 3070 of the base 3010 where carrier tile 601 is in its secured position. The needle apparatus 2000 feeds through the tile carrier 601 and exits out the loading channel exit hole 3053. Once the tip of the needle 2010 of the needle apparatus extends through the exit hole 3053 the needle 2010 is grasped with a needle-holder and pulled through until the thread 2020 provides a visual determination that the carrier is loaded properly and the seeds are in their proper location. When the seed is placed at the proper depth all of the offset color 2030 (such as purple) thread disappears inside of the tile 601 and loader device and the regular color thread 2025 is trimmed away.

FIG. 15 is a top plan view of an embodied gore carrier 1201 similarly shown in FIGS. 10A and 10B when placed in the loading bed 3070 of loader device 3000 of FIG. 13. FIG. 15 shows the gore 1201 is placed within the loading bed 3070 portion of the loader 3000. The lid 3020 portion of the loader has been removed so that the gore 1201 is visible and one can see that the orientation lines 1255 of the gore 1201 aligns directly to the loading channel support structure 3055 such that when a needle loader enters through the proximal end loading channel 3051 and extends through the loading channel support structure 3055 and enters into the loading bed portion 3070 of the base 3010 where a carrier gore 1201 is in a secured position the loading needle enters into the predetermined placement on the gore 1201 based on dosimetry needs for treatment. The gore 1201 loaded the same as described for the tile 601 in FIG. 14. Once the gore 1201 is loaded, it may be trimmed along the trim lines 1259 present on the antipodal surface 1210 of the gore 1201 if necessary.

Application and Treatment with Customized Radionuclide Carrier Systems

The specialized carriers of the present invention provide for certain precise dimensions to allow the carriers to guide users (neurosurgeons, cardiothoracic surgeons, general surgeons, dermatologists, radiation oncologists, urological surgeons, veterinarians or other qualified providers) in maintaining precise and preplanned dosimetry needed to produce effective and safe outcomes.

The dosimetrically customizable implants of the present invention may be used as a means of treating, curing, ameliorating, or slowing the progression of various tumors of the body, including but not limited to; tumors of the central nervous system, head and neck, spine, soft tissues, bone, liver, lung, breast, skin, esophagus, stomach, intestines, colon, rectum, prostate, pancreas, retroperitoneal space, kidney, bladder, pelvis, ovary, cervix, fallopian tubes, uterus, and vagina.

The embodied carrier systems may be used in methods to facilitate intracavitary, intraluminal, interstitial, and external surface brachytherapy used with and without surgical resection of the tumors.

The embodied carrier systems may be used in methods specifically for treating extracranial, interstitial, intra-cavitary, surface or visceral site irradiation treatment of various primary and metastatic tumors.

The custom radionuclide carrier systems of the present invention may be used for implantation within the central nervous system and include a radiolabeled implant for interstitial implantation comprising a substantially rigid implantable matrix design to be a carrier for radioactive seeds to produce a dosimetrically customizable implant in real-time for each patient and lesion.

The dosimetrically customizable implants described herein may be used to treat, cure ameliorate or slow-down the progression and thus provide a defense against various brain tumors including but not limited to, meningioma, glioma, metastatic cancer and craniopharyngioma.

The rigid implantable matrix designs may include a design wherein the matrix is an implantable tile. The methods of above with the use of low-energy radioactive seeds Cs 131, Ir 192, I 125, Pd 103 or other isotopes to be used intraoperative following surgical resection as a permanent implant.

The types of tumors to be treated include primary, secondary and recurrent tumors involving the central nervous system.

A program/spreadsheet/nomogram to guide planning implants and ordering of seeds/tiles based on preoperative lesion size, shape, location, histology and number may be provided to assist the user when using the present carrier systems.

Figure 16:
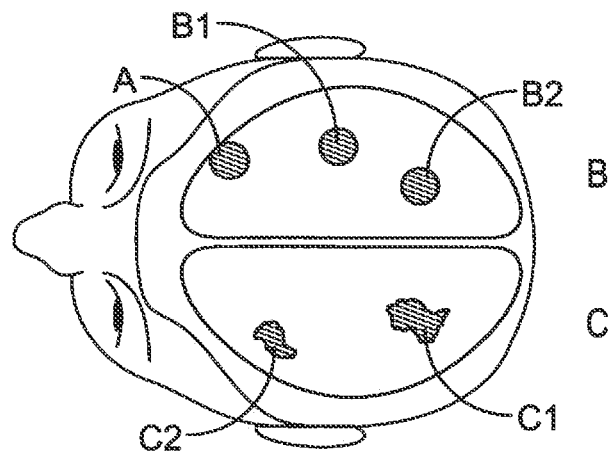
FIG. 16 illustrates exemplary preoperative shapes and locations and tumors to be treated with one or more of the embodied devices of the present invention.
Figure 17:
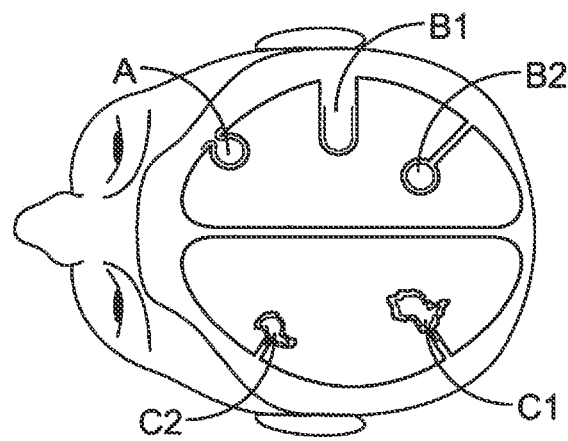
FIG. 17 illustrates exemplary the shape and location of various post-operative cavities to be treated with one or more of the embodied devices of the present invention.
Figure 18A:
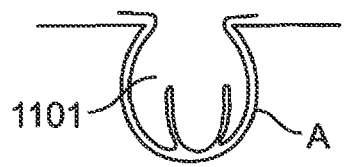
FIG. 18 comprises FIGS. 18A, 18B, 18C, 18D and 18E each show different applications and configurations of the carrier systems for treating variable target treatment areas.
Figure 18B:
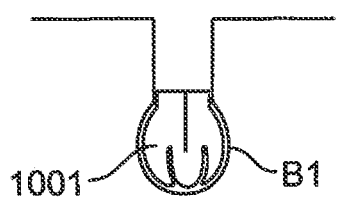
Figure 18C:
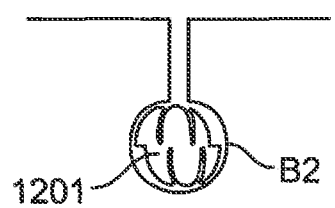
Figure 18D:
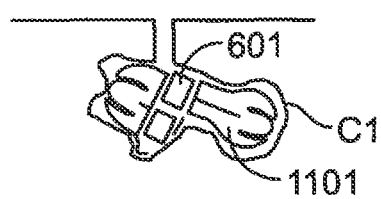
Figure 18E:

FIGS. 16-18 demonstrate some of the exemplary surgical applications and customization process that can be achieved with the tile carriers or the gore carriers or combinations of the two carriers.

FIG. 16 shows the pre-operation shape and locations of tumors in three common places and geometries. In position A the tumor is rounded in shape and located at or very near the brain surface. In position B there are two tumors shown as rounded in shape but the tumors have different accessibilities in that the tumors may be deeper into the brain tissue for B1 than B2. In position C there are two variable lesions C1 and C2 where there is an irregular tumor bed shape and the lesion may be in any variety of shape and depth.

FIG. 17 shows the post-operation cavity shape location associated with each of the above pre-op positions. The position A is considered concave in shape with a surface flair. The position B1 post-op is considered concave deep and stovepipe. The position B2 post-op is considered a Bi-concave bed. The position C1 is now considered regular with an irregular bed. And position C2 is considered irregular, with an irregular bed and variations.

For each of these tumors/tumor beds there is a high variability of size shape and location but the options for the surgeon with the carriers of the present invention are almost unlimited in creating coverage possibilities with the tiles or gores or a combination of the two.

FIG. 18 shows embodied carrier solutions for each of the above tumor beds. The carrier solution for the position A tumor bed that is considered concave in shape with a surface flair would be for the user to use a petal and flap gore with an extended flap such as gore carrier 1101 shown in FIG. 9B. The carrier solution for the position B1 post-op which is considered concave deep and stovepipe would be for the user to use a petal and flaps gore such as the gore carrier 1001 shown in FIG. 9A. The carrier solution for the position B2 post-op which is considered a Bi-concave bed would be for the user to use a double petal gore such as the gore carrier 1201 shown in FIG. 10. The carrier solution for the position C1 which is considered regular with an irregular bed would be for the user to use one or more gores to fit and then additional tile configurations to fill as needed. The carrier solution for the position C2 which is considered irregular, with an irregular bed and variations would be for the user to use just the tile carriers because of the lack of space for a full gore implant.

This invention would also be useful in veterinary oncology, either alone or in combination with surgery. Fractionated radiation therapy is logistically more difficult and costly in animals, which require anesthesia prior to delivery of each fraction. Customizable BT, utilizing this invention, will enable delivery of effective and efficient treatment in properly selected tumors.

Although the invention has been described with reference to the above example, it will be understood that modifications and variations are encompassed within the spirit and scope of the invention. Accordingly, the invention is limited only by the following claims.

What is claimed is:

1. A radiation treatment system comprising:
   planning software, spreadsheet or nomogram adapted to guide a user in planning radiation treatment of mammalian tissue, the planning software, spreadsheet or nomogram providing the user with at least a quantity of radioactive seeds to be used in the radiation treatment based on one or more of a preoperative shape of a treatment area, size of a lesion within the treatment area, anatomical location of the treatment area, or histology of the mammalian tissue;
   a plurality of radioactive seed carriers as determined by the planning software, spreadsheet or nomogram, each of the plurality of radioactive seed carriers comprising a biocompatible material having a top surface, an opposing bottom surface, and a thickness of between four and seven millimeters therebetween, wherein the top surface and the bottom surface are substantially rectangular with each side of the rectangle having a length of at least one centimeter;
   a plurality of radioactive seeds encased within one or more titanium layers, one or more of the plurality of the radioactive seeds configured for implantation into respective radioactive seed carriers, each of the radioactive seeds comprising Cesium-131 emitting radiation configured to kill living cells; and
   a loading device comprising:
      a planar surface defining a loading bed perpendicular to sides of the loading device and adapted to support one of the plurality of radioactive seed carriers abutting a first side of the sides of the loading device; and
      a guide channel disposed in the first side of the sides of the loading device, the guide channel configured to receive and direct a guide tool parallel to the planar surface, the a guide tool configured to move one or more of the plurality of radioactive seeds into and at least partially through the radioactive seed carrier supported on the loading bed of the loading device;
   wherein the plurality of radioactive seed carriers each embedding respective radioactive seeds are configured for custom placement with reference to one another near or in the treatment area in order to customize radiation delivered from the embedded radioactive seeds to the treatment area and minimize radiation delivered outside the treatment area.

2. The radiation treatment system of claim 1, wherein an amount of radiation emitted from the bottom surface of the biocompatible material of the radioactive seed carriers is greater than an amount of radiation emitted from the top surface of the biocompatible material of the radioactive seed carriers.

3. The radiation treatment system of claim 2, wherein each of the radioactive seed carriers comprises a textural feature on either the top surface or the bottom surface such that the top surface and bottom surface are identifiable by touch of a user.

4. The radiation treatment system of claim 1, wherein at least some of the plurality of radioactive seed carriers include one or more indicator lines marking locations to cut the radioactive seed carriers in order to create a smaller sized radioactive seed carrier.

5. A radiation treatment apparatus comprising:
  a radioactive seed carrier comprising a biocompatible material configured to embed a radioactive seed, the radioactive seed carrier having a top surface;
  an opposing bottom surface; and
  a thickness of between two and seven millimeters therebetween;
  wherein the top surface and the bottom surface are substantially rectangular with each side of the rectangle having a length of at least one centimeter;
  a radioactive seed adapted for implantation into the radioactive seed carrier, the radioactive seed comprising Cesium-131 emitting radiation configured to kill living cells; and
  a loading device configured to receive the radioactive seed carrier, the loading device comprising:
    a first side;
    a loading bed perpendicular to the first side of the loading device, the loading bed defining a planar surface adapted to support the radioactive seed carrier in abutting relationship to the first side of the loading device during loading of the radioactive seed into the radioactive seed carrier; and
    a guide channel disposed through the first side of the loading device, the guide channel configured to receive and direct an elongate guide tool parallel to the planar surface through the guide channel and at least partially into the thickness of the radioactive seed carrier supported on the loading bed of the loading device;
  wherein the radioactive seed carrier embedding the radioactive seed, after removal from the loading device, is configured for placement in a treatment area of mammalian tissue.

6. The radiation treatment apparatus of claim 5, wherein the elongate guide tool is a needle.

7. The radiation treatment apparatus of claim 6, wherein the radioactive seed is attached to a thread and the thread is attached to the needle such that movement of the needle through the guide channel and the thickness of the radioactive seed carrier results in movement of the thread and the radioactive seed into the radioactive seed carrier.

8. The radiation treatment apparatus of claim 5, wherein an entire length of the elongate needle is straight.

9. A radiation treatment apparatus comprising:
  a biocompatible carrier adapted for placement in mammalian tissue after embedding a radioactive seed therein, the carrier having a top surface;
  an opposing bottom surface; and
  a side between the top surface and bottom surface having a thickness of between two and seven millimeters;
  a radioactive seed adapted for embedding in the carrier, the radioactive seed comprising Cesium-131; and
  a loading device configured to support the radioactive seed carrier while embedding the radioactive seed into the carrier, the loading device comprising:
    a first side;
    a second side spaced apart from and the first side;
    a planar surface between and perpendicular to the first and second sides of the loading device, the planar surface adapted to support the carrier during embedding of the radioactive seed into the carrier; and
    a guide channel disposed through one of the first or second sides of the loading device, the guide channel configured to receive and direct a needle substantially parallel to the planar surface, through the guide channel, and at least partially into the side of the carrier while the carrier is supported on planar surface of the loading device and abutting the guide channel;
  wherein the carrier embedding the radioactive seed, after removal from the loading device, is configured for placement in a treatment area of mammalian tissue.

10. The radiation treatment apparatus of claim 9, wherein the guide channel is a first guide channel disposed through the first side of the loading device and the loading device comprises a second guide channel disposed through a lid of the loading device.

11. The radiation treatment apparatus of claim 9, wherein the radioactive seed is attached to a thread and the thread is attached to the needle.

12. The radiation treatment apparatus of claim 9, wherein the radioactive seed further comprises at least one titanium layer.

13. A radiation treatment apparatus comprising:
  a radioactive seed carrier comprising a biocompatible material configured to embed a radioactive seed, the radioactive seed carrier having
    a top surface;
    an opposing bottom surface; and
    a thickness of between two and seven millimeters therebetween;
    wherein the top surface and the bottom surface are substantially rectangular with each side of the rectangle having a length of at least one centimeter;
  a radioactive seed adapted for implantation into the radioactive seed carrier, the radioactive seed comprising Cesium-131 emitting radiation configured to kill living cells; and
  a loading device configured to receive the radioactive seed carrier, the loading device comprising:
    a first side;
    a second side spaced apart from the first side;
    a third side between and connecting the first and second sides;
    a loading bed perpendicular to the first, second, and third sides of the loading device, the loading bed defining a planar surface adapted to support the radioactive seed carrier in abutting relationship to the third side of the loading device during loading of the radioactive seed into the radioactive seed carrier; and
    a guide channel disposed through the third side of the loading device, the guide channel configured to receive and direct an elongate guide tool parallel to the planar surface through the guide channel and at least partially into the thickness of the radioactive seed carrier supported on the loading bed of the loading device;

wherein the radioactive seed carrier embedding the radioactive seed, after removal from the loading device, is configured for placement in a treatment area of mammalian tissue.

14. The radiation treatment apparatus of claim 13, wherein the elongate guide tool is a needle.

15. The radiation treatment apparatus of claim 13, further comprising a second guide channel disposed through the third side of the loading device, the second guide channel configured to receive and direct the elongate guide tool parallel to the planar surface through the second guide channel and at least partially into the thickness of the radioactive seed carrier supported on the loading bed of the loading device.

* * * * *